United States Patent [19]

Byalko et al.

[11] 4,073,183

[45] Feb. 14, 1978

[54] PNEUMATIC DETECTOR OF GAS AND VAPOR CONTAMINANTS IN ATMOSPHERE OF INDUSTRIAL BUILDINGS

[76] Inventors: Mikhail Vladimirovich Byalko, Studeny proezd, 38, korpus 2, kv. 388; Elena Viktorovna Kirko, ulitsa Udaltsova, 10, kv. 77; Rafael Shliomovich Perlovsky, Sirenevy bulvar, 27, korpus 2, kv. 113; Vadim Jurievich Ryzhnev, Ryazansky prospekt, 95 korpus 4, kv. 20, all of Moscow, U.S.S.R.

[21] Appl. No.: 706,791

[22] Filed: July 19, 1976

[51] Int. Cl.² .............................................. G01N 33/00

[52] U.S. Cl. .......................................... 73/23; 116/65

[58] Field of Search .............................. 73/23; 116/65

[56] References Cited

U.S. PATENT DOCUMENTS

| | | | |
|---|---|---|---|
| 3,273,377 | 9/1966 | Testerman et al. | 73/23 |
| 3,592,042 | 7/1971 | Martinez | 73/23 |

*Primary Examiner*—Herbert Goldstein

*Attorney, Agent, or Firm*—Lackenbach, Lilling & Siegel

[57] ABSTRACT

A pneumatic detector comprising a jet sensor, a pressure comparator, a vacuum former and a vacuum pump. The feed pipe of the jet sensor communicates with reference and analyzed gas channels through a first switching element.

The pneumatic detector according to the invention makes it possible to determine the different concentrations of the dangerous vapor and gas contaminants in the air of industrial buildings with a high degree of accuracy and reliability.

35 Claims, 3 Drawing Figures

Figure 1:
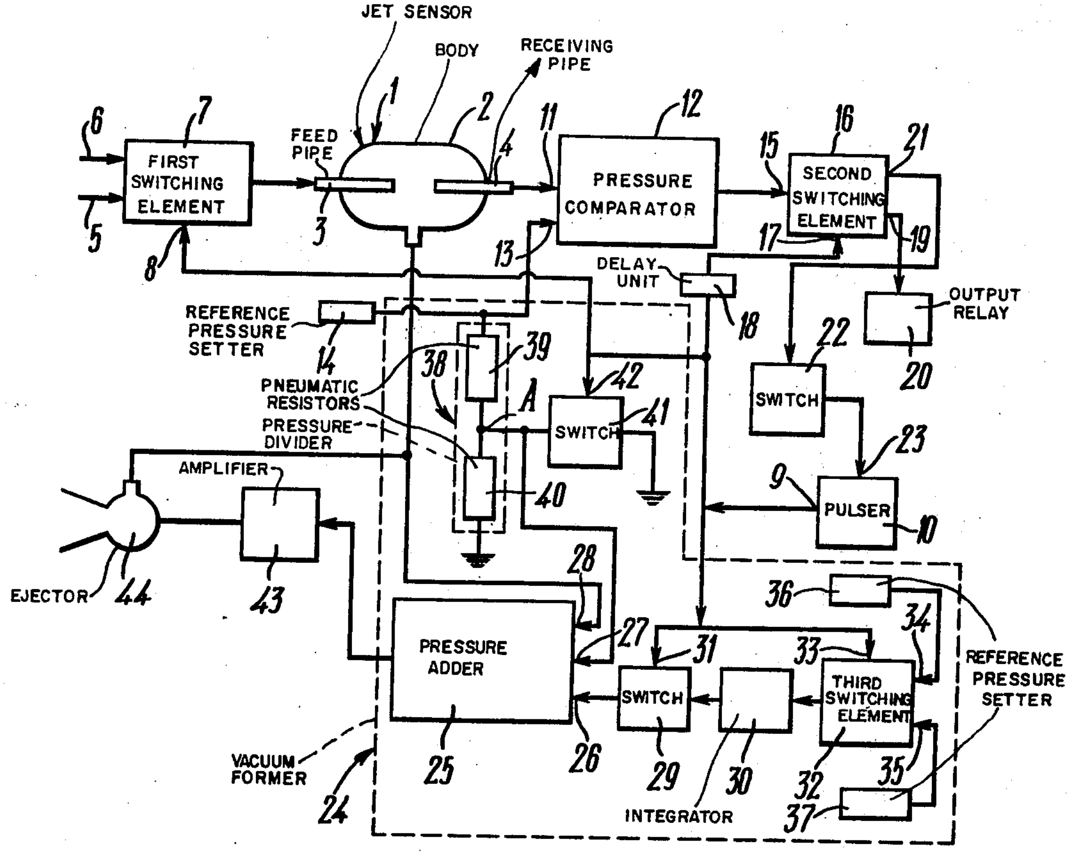

PNEUMATIC DETECTOR OF GAS AND VAPOUR CONTAMINANTS IN ATMOSPHERE OF INDUSTRIAL BUILDINGS

The present invention relates to jet-type pneumatic automatic control devices and more particularly it relates to a pneumatic detector of gas and vapour contaminants in the atmosphere of industrial buildings.

The invention can be employed in automatic systems for controlling and detecting gas and vapour contaminants in the air of industrial buildings. It will be used most sucessfully in the protection systems of various installations and workshops for detecting the preexplosive concentrations of various combustible gases and vapours in the air of industrial buildings.

Widely and long known in the prior art are thermochemical detectors of preexplosive concentrations of various combustible gases and vapours in the air of industrial buildings. These detectors comprise a catalyst for burning the combustible gases contained in the analyzed air. The amount of heat liberated by the catalyst and, consequently, the catalyst temperature vary with the concentration of these gases in the air. The temperature is usually measured by resistance thermometers which themselves serve, in the majority of cases, as catalysts.

The above-mentioned detectors allow control of the concentrations of combustible gases within 5 to 50% of the lower explosion limit. Such sensitivity of the thermochemical detectors ensures their efficient employment in the fire and explosion protection systems of industrial buildings. However, in view of their operating principle, these detectors require equipment with special complicated devices to make them explosion-proof.

The provision of such complicated explosion-protecting devices is likewise imperative for the other known detectors, such as plasma-ionization and spark types.

Accordingly, it is expedient to detect the preexplosive concentrations of gases with the aid of said pneumatic gas detectors which are now being used on an ever-growing scale owing to the advancements in the jet technology. The operating principle of these gas detectors is based on measuring certain physical parameters whose dependence on the chemical composition of the analyzed substance is precisely determined. These parameters are volume, partial pressure, density of gas mixture, etc.

However, the above-mentioned pneumatic gas detectors cannot be used to indicate the preexplosive concentrations of combustible gases and vapours in the air since for the majority of substances these concentrations do not exceed 1–1.5 vol.-% while the level of sensitivity of these gas detectors to the changes in the composition of gases obtained so far is usually 10 vol-% and higher.

This can be attributed to the fact that these pneumatic gas detectors rely mostly on the quantitative changes in the parameters of flow in jet sensors while retaining the qualitative characteristics of said flow. The appearance of the analyzed concentration causes but an insignificant change in the physical properties of the analyzed medium. For axample, when the concentration of acetylene in the air reaches 20% of its lower explosion limit, the density of air changes by 0.057% and its viscosity by 0.353%. As a result, the output signal of the sensor in any one of the known pneumatic gas detectors supplied with the above-mentioned medium changes by the value which is commensurate with the permissible noise level of the modern pneumatic automation devices.

The above considerations have necessitated the provision of a pneumatic detector of preexplosive concentrations. The high sensitivity required for solving this problem could be obtained in such a detector by two methods:

by providing an independent amplifier with a high coefficient of amplification which, however, is not economical;

by a more economical method, i.e. by providing a sensor possessing a higher sensitivity to changes in the compositon of the working medium within a certain zone of its static curve which presents the relationship between the values of the sensor output and input signals. This zone proved to be the zone of the static curve of the jet sensor comprising the feed and receiving pipes which corresponds to the conditions of transition from the laminar to turbulent flow of the analyzed gas, the sensor in this zone possessing a high coefficient of amplification.

The method of detecting the preexplosive concentrations of combustible gases in air according to the invention utilizes the dynamic effect accompanied by the qualitative changes in the flow of the gas jet caused by the changes in the physical properties of the gas flowing through the feed pipe.

This method has been realized in the pneumatic detector of gas and vapour contaminants in the atmosphere of industrial buildings. This pneumatic detector comprises a jet sensor made in the form of feed and receiving pipes accommodated in the body. The feed pipe communicates with channels of the analyzed and reference gases by means of a first switching element. The control inlet of the switching element is connected to a generator which sets the operational mode of the detector.

The receiving pipe of the jet sensor communicates with one of the inlets of a pressure comparator whose other inlet is connected to a reference pressure setter. The setter is made in the form of a throttle-type divider communicating with an ejector. The outlet of the pressure comparator is connected by a second switching element with an output relay and a vacuum former. The control inlet of the second switching element is connected to the outlet of the timing signal generator.

The vacuum former in the given detector is made in the form of a consecutively-connected throttle and pneumatic container. The throttle is connected to the second switching element while the container is connected with the ejector via an amplifier. The ejector communicates with the inside space of the jet sensor.

However, the known pneumatic detector has insufficiently high metrological characteristics. This is caused by the following factors.

In the known pneumatic detector the analysis of the concentration of various gas and vapour contaminants in the air is preceded by the so-called correction of the working point. The term "working point" in this case should be understood as the point on the static curve of the jet sensor which represents the dependence of the dynamic head in the receiving pipe upon the difference of pressures in the feed pipe, said point being located on the steepest zone of the curve corresponding to the transition from the laminar to turbulent flow of gas in the gap between the feed and receiving pipes. This correction of the working point equalizes the pressures entering the inlets of the pressure comparator from the receiving pipe and the reference pressure setter. During this correction the pneumatic detector develops natural vibrations because the outlet of the pressure comparator is put in communication with the ejector by means of the second switching element and the vacuum former. These natural vibrations lead to an unstable functioning of the detector and erroneous operations. The amplitude of the natural vibrations grows with the increase in the steepness of the static curve. Due to this fact it is impossible to use the jet sensors with the steepest static curve, i.e. with the greatest sensitivity to the gas and vapour contaminants in the atmosphere being analyzed.

At the same time the known detector cannot be set to indicate different concentrations of gas and vapour contaminants in the air of industrial buildings. This must be attributed to the fact that the above-described detector has no provision for changing the position of the working point or for changing the concentration at which the detector will operate.

Besides, the life of the known pneumatic detector is comparatively short. This happens because the ratio of the time spent for producing the pneumatic signals "1" and "0" at the generator output corresponding to the correction of the working point and for direct analysis of the concentration of contaminants in the analyzed gas does not exceed 1:10. As a result, the detector correction cycle lasting 5–7 *s* is repeated every minute though according to the operating conditions the frequency of these correction cycles can be considerably lower.

An object of the present invention is to improve the metrological characteristics of the pneumatic detector of gas and vapour contaminants in the air of industrial buildings.

Another object of the present invention is to provide a pneumatic detector capable of being adjusted for determining different concentrations of gas and vapour contaminants in the air of industrial buildings.

Still another object of the present invention is to extend the service life of the pneumatic detector.

These objects are accomplished by providing a pneumatic detector of gas and vapour contaminants in the air of industrial buildings which comprises a jet sensor made in the form of a feed pipe, which is accommodated in the body and which communicates with reference and analyzed gas channels through a first switching element whose control inlet is connected to the outlet of the element intended to set the operational mode, and a receiving pipe which communicates with one of the inlets of a pressure comparator whose other inlet communicates with a reference pressure setter whose outlet communicates with the outlet of a relay and with a vacuum former through a second switching element whose control inlet is connected with the outlet of the mode-setting element while the vacuum former communicates via an amplifier with a vacuum pump communicating with the jet sensor according the invention, the vacuum former comprises a pressure adder whose first inlet communicates with the jet sensor while its outlet communicates with the vacuum pump; a pressure divider whose inlet communicates with the reference pressure setter, whose outlet communicates with whose atmosphere and the central point communicates with the second inlet of the pressure adder; a first switch putting the central point of the pressure divider in communication with the atmosphere; two additional reference pressure setters; an integrator; a third switching element whose inlets are connected to whose reference pressure setters and the outlet is connected to a integrator inlet; the second switch intended to connect the integrator outlet to the third inlet of the pressure adder; an operating mode-setting element being made in the form of a pulser whose control inlet is connected by a third switch to the outlet of the second switching element while its outlet communicates with the control inlet of the second switching element through a delay unit and is directly connected to the control inlets of the first and second switches and of the third switching element.

The above-described pneumatic detector has higher metrological characteristics than those of the known pneumatic detector. This is achieved because operation of the pneumatic detector according to the invention is stable in spite of the fact that it utilizes jet sensors with a steep static curve and, consequently, with a high sensitivity. Stable operation of the detector during correction of the working point is ensured because the vacuum former comprises a pressure adder whose inlet communicates with an integrator which provides for a smooth increase of vacuum in the jet sensor body. Owing to the communication between the outlet of the pressure comparator and the control inlet of the pulser through the second switching element and the third switch, and also due to the communication between the pulser outlet and the second switch, the pressure adder memorizes the required vacuum which corresponds to the working point.

At the same time the pneumatic detector according to the invention is capable of being adjusted for detecting different concentrations of contaminants in the air. This is possible due to the provision of the pressure divider in the vacuum former, the central point of said pressure divider being in communication with one of the inlets of the pressure adder and with the atmosphere through the first switch. Depending on the relationship of the pneumatic resistances of the pressure divider the vacuum memorized by the pressure adder changes and so does the concentration of gas and vapour contaminants in the analyzed gas at which the detector will operate.

In addition, the above-described pneumatic detector has an increased service life over that of the known detector. This is achieved by providing it with a pulser which sets the operational mode and has the above-mentioned connections. Thus, it becomes possible to set any required ratio of the time required for correcting the working point to the time required for direct analysis of the concentration of gas and vapour contaminants in the analyzed air. As a result, the frequency of corrections can be considerably reduced thereby extending the detector life.

Figure 2:
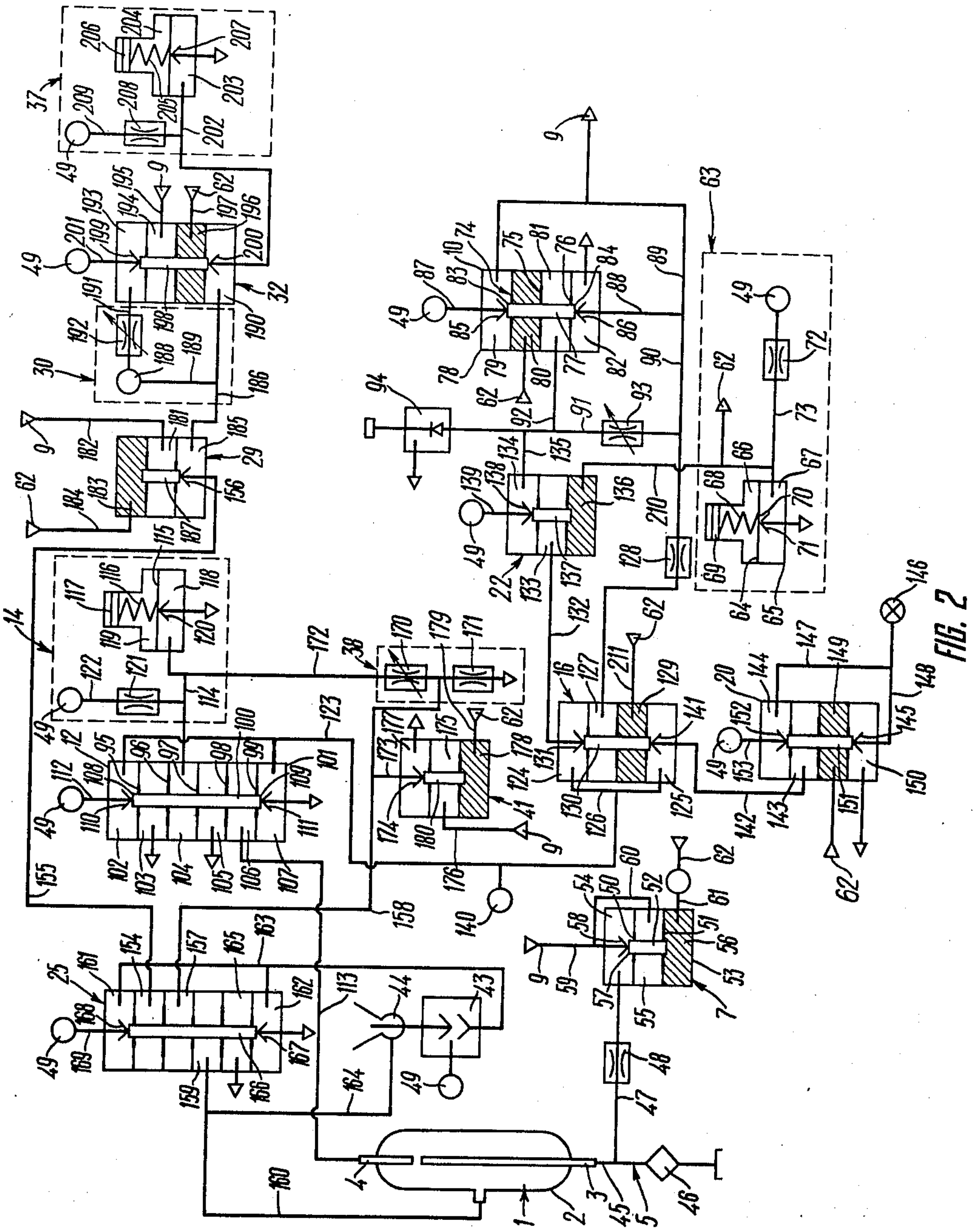
Figure 3:
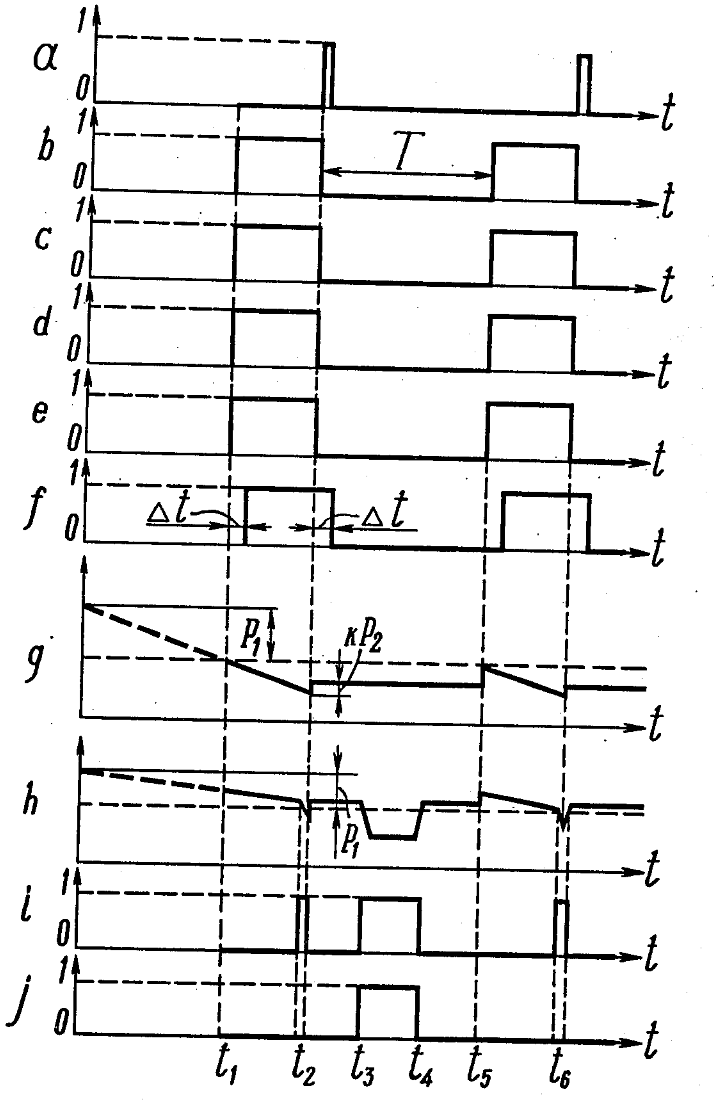

Other objects and advantages of the present invention will become apparent from the example of its realization described below and from the accompanying drawings in which:

FIG. 1 is a block diagram of the pneumatic detector of gas and vapour contaminants in the air of industrial buildings according to the invention;

FIG. 2 is a schematic diagram of the pneumatic detector according to the invention; and FIGS. 3 *a, b, c, d, e, f, g, h, i, j* are time diagrams of the pneumatic signals at the outlets of the third switch and pulser, at the inlets of the first and second switches, third switching element, second switching element, in the body of the jet sensor and at the outlets of the jet sensor, pressure comparator and output relay.

The pneumatic detector of gas and vapour contaminants in the air of industrial buildings comprises a jet sensor 1 (FIG. 1). This sensor 1 is comprised of a feed pipe 3 and a receiving pipe 4, both accommodated in a body 2. The feed pipe 3 communicates with the analyzed gas channel 5 and the reference gas channel 6 via a switching element 7. The gas to be analyzed is the air of an industrial building. The standard gas is constituted of pure air. The control inlet 8 of the switching element 7 is connected to the outlet 9 of a pulser 10. The receiving pipe 4 communicates with the inlet 11 of a pressure comparator 12. The inlet 13 of the pressure comparator 12 communicates with a reference pressure setter 14. The outlet of the pressure comparator 12 is connected to the inlet 15 of the switching element 16. The control inlet 17 of the switching element 16 is connected to the outlet 9 of the pulser 10 via a delay unit 18. One outlet 19 of the switching element 16 is connected to an output relay 20 while its other outlet 21 is connected by a switch 22 to the control inlet 23 of the pulser 10.

The outlet 9 of the pulser 10 is connected to a vacuum former 24. The vacuum former 24 takes the form of a pressure adder 25 having three inlets 26, 27 and 28. The inlet 26 of the pressure adder 25 is connected by a switch 29 with an integrator 30. The control inlet 31 of the switch 29 is connected to the outlet 9 of the pulser 10. The inlet of the integrator 30 is connected to the outlet of a switching element 32 which has three inlets 33, 34 and 35. Its control inlet 33 is connected to the outlet of the pulser 10. The inlets, 34 and 35 are connected, respectively, to the reference pressure setters 36 and 37.

The inlet 27 of the pressure adder 25 communicates with the central point A of the pressure divider 38 consisting of two pneumatic resistances 39 and 40. The central point A of the pressure divider 38 is also in communication with the atmosphere through a switch 41 whose control inlet 42 communicates with the outlet 9 of the pulser 10. The inlet of the pressure divider 38 communicates with the reference pressure setter 14 while its outlet is vented to the atmosphere.

The inlet 28 of the pressure adder 25 communicates with the inside space of the body 2 of the jet sensor 1.

The outlet of the pressure adder 25 communicates via an amplifier 43 with an ejector 44 which is also in communication with the body of the jet sensor 1.

The analyzed gas channel 5 is constituted by a pipe 45 (FIG. 2) communicating with the feed pipe 3 and provided with a filter 46. The standard gas channel 6 (FIG. 1) is constituted by a pipe 47 (FIG. 2) communicating with the feed pipe 3, comprising a throttle 48 and being connected to the first switching element 7 which, in turn, is in communication with a compressed air source 49 through the pulser 10.

The throttle 48 has a conventional design and is intended to limit the consumption of flow of pure air.

The switching element 7 is made in the form of two membranes 50 and 51 of different areas, rigidly interconnected by a rod 52 and forming three chambers 54, 55 and 56 in a common casing 53.

The butt end of the rod 52 located in the chamber 54 is represented as a shutter 57 for the nozzle 58. The nozzle 58 communicates with the pulser outlet 9 through a pipe 59. The chamber 55 serving as the control inlet 8 (FIG. 1) of the switching element 7 is connected by pipes 60 (FIG. 2) and 59 with the pulser outlet 9. The chamber 56 is connected by a pipe 61 with the outlet 62 of a pressure head setter 63.

The pressure head setter 63 comprises a membrane 64 accommodated in a casing 65 and dividing it into two chambers 66 and 67. The chamber 66 accommodates a spring 68 connected with the membrane 64 and the screw 69 used to adjust the spring tension. The rigid center of the membrane 64 serves as a shutter 70 for the nozzle 71. The nozzle 71 communicates with the atmosphere. The pressure head setter 63 also comprises a constant-flow throttle 72 installed on a pipe 73 which communicates with the chamber 67 and the compressed air source 49.

The pulser 10 which sets the operational mode of the pneumatic detector comprises three membranes 74, 75 and 76 rigidly interconnected by a rod 77 and forming four chambers 79, 80, 81 and 82 in a common casing 78. The butt ends of the rod 77 serve as shutters 83 and 84 for nozzles 85 and 86, respectively. The nozzle 85 communicates by a pipe 87 with the compressed air source 49. The nozzle 86 communicates with the chamber 79 through pipes 88 and 89. The nozzle 86 is also connected by pipes 88, 90, 91, 92 and a variable-resistance throttle 93 with the chamber 81 and a button 94. The throttle 93 and button 4 are of a known design.

The button 94 allows the working point of the detector to be adjusted at any time at the operator's will.

The chamber 80 is in communication with the outlet 62 of the pressure head setter.

The pressure comparator 12 is made in the form of five membranes 95, 96, 97, 98, 99 rigidly interconnected by a rod 100 and forming six chambers 102, 103, 104, 105, 106, 107 in a casing 101. The butt ends of the rod 100 serve as shutters 108 and 109 for nozzles 110 and 111, respectively. The nozzle 110 communicates by a pipe 112 with the compressed air source 49. The nozzle 111 is vented to the atmosphere and so are the chambers 103 and 105. One inlet 11 (FIG. 1) of the pressure comparator 12 is constituted by the inlet of the chamber 106 (FIG. 102) which communicates through a pipe 113 with the receiving pipe 4. Its other inlet 13 (FIG. 1) is constituted by the inlet of the chamber 104 (FIG. 2) which is in communication with the reference pressure setter 14 through a pipe 114.

The design of the reference pressure setter 14 is similar to that of the pressure head setter 63 described above. It has a membrane 115, a spring 116, a screw 117, chambers 118 and 119, a nozzle 120 communicating with the atmosphere and a constant-flow throttle 121 installed on the pipe 122 which communicates with the compressed air source 49. The chamber 118 communicates with the chamber 104 of the pressure comparator 12 and the chamber 119 communicates with the atmosphere.

The outlet of the pressure comparator 12 is constituted by the outlet from the chambers 102 and 107 which communicate with each other through a pipe 123 connected to the inlet 15 (FIG. 1) of the switching element 16. The design of the switching element is similar to that of the pulser 10 described above. Its inlet 15 is constituted by the inlet into the chambers 124 (FIG. 2) and 125 which are in communication through a pipe 126. The control inlet 17 (FIG. 1) of the switching element 16 is constituted by the inlet into the chamber 127 (FIG. 2) which is connected to the outlet 9 of the pulser 10 through the pipe 90 which includes a throttle 128. The constant-flow throttle 128 functions as the delay unit 18 (FIG. 1). The delay time depends on the pneumatic resistance of the throttle 128 (FIG. 2).

The chamber 129 communicates with the outlet 62 of the pressure head setter.

The switching element 16 is provided with a rod 130. The nozzle 131 serving as the outlet 21 (FIG. 1) of said switching element 16 communicates through a pipe 132 (FIG. 2) with the chamber 133 of the switch 22.

The design of the switch 22 is similar to that of the switching element 7 described above. Its chamber 134 communicates through pipes 135, 91 and 92 with the chamber 81 of the pulser 10, the inlet of said chamber functioning as the control inlet 23 (FIG. 1) of the pulser 10. The chamber 136 (FIG. 2) communicates with the outlet 62 of the pressure head setter. The switch 22 comprises a rod 137. The nozzle 138 communicates through a pipe 139 with the compressed air source 49.

The pipe 123 is provided with a pressure gauge 140 intended to check the operation of the pneumatic detector.

The nozzle 141 which serves as the outlet 19 (FIG. 1) of the switching element 16 communicates by a pipe 142 (FIG. 2) with the chamber 143 of the output relay 20. The design of the output relay 20 is similar to that of the switching element 16. Its chamber 144 communicates with a nozzle 145 and with a pneumatic indicator 146 through pipes 147 and 148. The pneumatic indicator 146 is of a known design. The chamber 149 communicates with the outlet 62 of the pressure head setter. The chamber 150 communicates with the atmosphere.

The relay 20 comprises a rod 151. A nozzle 152 communicates through a pipe 153 with the compressed air source 49.

The pressure adder 25 of the vacuum former 24 is similar in design to the above-described pressure comparator 12. The inlet 26 (FIG. 1) of the pressure adder 25 is constituted by the inlet into the chamber 154 (FIG. 2) which communicates with the nozzle 156 of the switch 29 through a pipe 155. The inlet 27 (FIG. 1) is constituted by the inlet into the chamber 157 (FIG. 2) which communicates with the central point A of the pressure divider 38 through a pipe 158. The inlet 28 (FIG. 1) of the pressure adder 25 is the inlet into the chamber 159 (FIG. 2) which communicates with the inside space of the body 2 of the jet sensor 1 through a pipe 160. The outlet of the pressure adder 25 is formed by the outlet from the chambers 161 and 162 which are intercommunicated through a pipe 163 which is connected to the ejector 44 by the amplifier 43. The amplifier 43 and ejector 44 are of a conventional design. The ejector 44 communicates with the chamber 159 of the pressure adder 25 via a pipe 164.

The chamber 165 communicates with the atmosphere. The pressure adder 25 has a rod 166. The nozzle 167 is vented to the atmosphere while the nozzle 168 communicates with the compressed air source 49 through a pipe 169.

The pressure divider 38 is made in the form of two consecutively connected throttles 170 and 171. The throttle 170 comprises a variable pneumatic resistance.

The inlet of the pressure divider 38 communicates through pipes 172 and 114 with the chamber 118 of the reference pressure setter 14. The outlet of the pressure divider 38 communicates with the atmosphere. The central point A of the pressure divider 38 communicates with the nozzle 174 of the switch 41 through pipes 158 and 173. The switch 41 is similar in design to the above-described switch 22. The control inlet 42 (FIG. 1) of the switch is formed by the inlet into the chamber 175 (FIG. 2) which communicates with the pulser outlet 9 via a pipe 176. The chamber 177 of the switch 41 is vented to the atmosphere whereas the chamber 178 is in communication with the outlet 62 of the pressure head setter through a pipe 179. The switch has a rod 180.

The switch 29 is similar in design to the switch 41 described above. Its control inlet 31 (FIG. 1) is formed by the inlet into the chamber 181 (FIG. 2) which is in communication with the pulser outlet 9 via a pipe 182. The chamber 183 is connected by a pipe 184 with the outlet 62 of the pressure head setter whereas the chamber 185 communicates through a pipe 186 with the integrator 30. The switch 29 has a rod 187.

The integrator 30 is made in the form of a pneumatic container 188 which communicates via pipes 189 and 186 with the chamber 185 of the switch 29 and with the chamber 190 of the switching element 32. The pneumatic container 188 also communicates with the chamber 193 of the switching element 32 through a pipe 191 which is provided with a throttle 192 with a variable pneumatic resistance.

The design of the switching element 32 is similar to that of the above-described switching element 16. Its control inlet 33 (FIG. 1) is formed by the inlet into the chamber 194 (FIG. 2) which communicates with the pulser outlet 9 through a pipe 195. The chamber 196 communicates through a pipe 197 with the outlet 62 of the pressure head setter. The switching element 32 has a rod 198 and two nozzles 199 and 200. The nozzle 199 communicates by a pipe 201 with the compressed air source 49 which serves as the reference pressure setter 36 (FIG. 1). The nozzle 200 (FIG. 2) communicates through a pipe 202 with the chamber 203 of the reference pressure setter 37.

The reference pressure setter 37 is similar to the setter 14. It has a chamber 204 accommodating a spring 205 and a screw 206, another chamber 203 accommodating a nozzle 207 which communicates with the atmosphere, and a throttle 208 which communicates through a pipe 209 with the compressed air source 49 and with the chamber 203.

The functioning of the pneumatic detector is explained in FIGS. 3 *a, b, c, d, e, f, g, h, i* and *j* in the form of time diagrams of the pneumatic signals at the outlets of the *s* switch 22 and pulser 10, at the inlets of the switching element 7, switches 29 and 41, switching element 32, switching element 16, in the body of the jet sensor 1 and at the outlets of the jet sensor 1, pressure comparator 12 and output relay 20.

In these time diagrams the time is laid off on the X-axis and pressure, and the Y-axis. The pneumatic signal "1" on the Y-axis corresponds to the pressure of air approximately equal to the pressure of the compressed air source 49. When the pressure of the source 49 is equal to $1.4 \pm 0.14$ kg/cm$^2$ the indicated air pressure is not under 1 kg/cm$^2$. The pneumatic signal "0" indicated on the Y-axis corresponds to the atmospheric pressure.

The above-described pneumatic detector for determining the gas and vapour contaminants in the air of industrial buildings operates as follows.

The detector functions in one of two modes, viz., correction of the working point which is effected when the jet sensor 1 (FIG. 1) is supplied with reference gas (in this case pure air) and direct determination of the concentration of gas and vapour contaminants in the analyzed gas (in this case, the air of the industrial building) supplied to the jet sensor 1.

The working point correction mode commences when the pneumatic signal "1" (FIG. 3b) appears at the outlet 9 of the pulser 10.

The signal "1" is produced at the outlet 9 (FIG. 2) of the pulser 10 either automatically or when the normally-closed button 94 is pressed by hand. When the button 94 is pressed by hand, the chamber 81 of the pulser 10 is put in communication through pipes 92 and 91 with the atmosphere and pressure in it becomes equal to zero.

In this case the pressure head (approximately 0.6 kg/cm$^2$) in the chamber 80 and the difference of the areas of the membranes 74, 75 and 76 creates a force which acts upon the rod 77 and brings it down. As a result, the shutter 83 opens the nozzle 85, the shutter 84 closes the nozzle 86 so that the chamber 79 and the outlet 9 of the pulser 10 are fed with compressed air from the source 49 at a pressure corresponding to the pneumatic signal "1".

The signal "1" appears automatically at the outlet 9 of the pulser 10 due to a drop of air pressure in the chamber 81 when the latter is emptied through the throttle 93, the open nozzle 86 and the chamber 82 into the atmosphere. The rod 77 goes down too and the signal "1" appears at the outlet 9 of the pulser 10. By adjusting the pneumatic resistance of the throttle 93 it is possible to change the time "T" (FIG. 3b) between the two adjacent correction cycles of the working point.

Thus, owing to the use in the pneumatic detector, according to the invention, of the pulser 10 in the operational mode setting element it becomes possible to reduce the frequency of working point corrections and, consequently, to extend the service life of the pneumatic detector.

When the pneumatic signal "1" (FIG. 3b) appears at the outlet 9 (FIG. 2) of the pulser 10 at the moment of time $t_1$ (FIG. 3j), the air at a pressure corresponding to this signal flows simultaneously through the pipes 59 and 60 (FIG. 2) into the chamber 55 of the switching element 7, through the pipe 195 into the chamber 194 of the switching element 32, through the pipe 176 into the chamber 175 of the switch 41, through the pipe 182 into the chamber 181 of the switch 29 and, with a certain time delay $\Delta t$, through the pipe 90 and throttle 128 into the chamber 127 of the switching element 16.

As a result, due to the difference between the pressure head in the chamber 56 and the pressure of air entering the chamber 55, and the difference in the areas of the membranes 50 and 51, the rod 52 in the switching element 7 goes down and opens the nozzle 58. The pure air from the compressed air source 49 flows from the outlet 9 of the pulser 10 through the open nozzle 58 into the chamber 57 and thence, via the pipe 47 and throttle 48, into the feed pipe 3 of the jet sensor 1. Inasmuch as the throttle 48 is set to pass more pure air than the amount of analyzed air drawn through the senser 1 by the ejector 44, there is no supply of analyzed air to the sensor 1 in the correction mode.

As the pneumatic signal "1" enters the chamber 194 of the switching element 32, the rod 198 goes down, closing the nozzle 200 and opening the nozzle 199. The compressed air flows from the source 49 through the pipe 201 into the chamber 193 wherefrom it passes into the pneumatic container 188 thus building up air pressure therein. By adjusting the throttle 192 it is possible to change the rate of increase of the air pressure in the pneumatic container 188.

As the pneumatic signal "1" enters the chamber 175 of the switch 41 the rod 180 goes down and opens the nozzle 174. As a result, the central point A of the pressure divider 38 is put in communication with the atmosphere through the pipes 158 and 173, and through the nozzles 174 and chamber 177 so that the air pressure in it becomes equal to zero. The pressure of air in the chamber 157 of the pressure adder 25 communicating through the pipe 158 with the central point A of the pressure divider 38 also drops to zero.

As the pneumatic signal "1" enters the chamber 181 of the switch 29, the rod 186 rises, opening the nozzle 156. The air begins flowing from the pneumatic container 188 and the open nozzle 156 through the pipe 155 into the chamber 154 of the pressure adder 25. The air pressure in the chamber 154 begins growing, the rod 166 goes down, the nozzle 168 opens partly, the chambers 161 and 162 are put in communication with the compressed air source 49 so that pressure in said chambers grows too. The air flows from these chambers 161 and 162 at a growing pressure through the pipe 163 and amplifier 43 to the ejector 44. Being in communication with the chamber 159, the ejector builds up a vacuum in said chamber, this vacuum being equal to the pressure in the chamber 154. Then this vacuum is conveyed into the body 2 of the jet sensor 1.

When the pneumatic signal "1" enters the chamber 127 (FIG. 2) of the switching element 16 through the throttle 128 with a certain time delay $\Delta t$ (FIG. 3f), the rod 130 of said element goes down, closing the nozzle 141 and cutting off the chambers 102 and 107 of the pressure comparator 12 from the chamber 143 of the output relay 20. This opens the nozzle 131 which puts the chambers 102 and 107 of the pressure comparator 12 in communication with the chamber 133 of the switch 22.

As the pneumatic container 188 of the integrator 30 is gradually filled with air from the source 49, the air pressure in said container will grow.

This will be accompanied by the corresponding increase of pressure in the chamber 154 of the pressure adder 25 communicating with said container 188, and, as a consequence, by an increase of the vacuum in the chamber 159 of the pressure adder 25 and in the body 2 of the jet sensor 1, said body communicating with said chamber 159. It can be seen in FIG. 3g that the absolute pressure in the body 2 drops. The absolute pressure at the outlet of the receiving pipe 4 of the jet sensor 1 and in the chamber 106 of the pressure comparator 12 drops too as shown in FIG. 3h.

When time $t_2$ comes (FIG. 3j) and the absolute pressure at the outlet of the receiving pipe 4 (FIG. 2) of the jet sensor sharply drops as shown in FIG. 3h due to, say, turbulization of the jet of pure air discharged from the receiving pipe 4 (FIG. 2), the vacuum at its outlet and in the chamber 106 of the pressure comparator 12 drops below the air pressure in its chamber 104. The pressure of air in the chamber 104 is adjusted by the reference pressure setter 14 which is done by tensioning the spring 116 with the screw 117.

As the air pressure in the chamber 104 grows higher than the vacuum in the chamber 106, the rod 100 goes down, closing the nozzle 111 and opening the nozzle 110. The chambers 102 and 107 communicate through the open nozzle 110 with the compressed air source 49 and the air pressure in these chambers becomes approximately equal to the supply pressure.

The air at the supply pressure flows from the chambers 102 and 107 through the pipe 123 into the chambers 124 and 125 of the switching element 16 and, through the open nozzle 131 and the pipe 132, into the chamber 133 of the switch 22. Owing to the fact that the pressure in the chamber 133 rises higher than the pressure in the chamber 136 communicating through the pipe 210 with the outlet 62 of the pressure head setter 63, the rod 137 goes down, opening the nozzle 138 and putting the compressed air source 49 in communication with the chamber 81 of the pulser 10. The rod 77 rises, closes the nozzle 85 and opens the nozzle 86. The chamber 79 and the outlet 9 of the pulser 10 are vented to the atmosphere through the pipe 89, open nozzle 86 and the chamber 82. The pneumatic signal "0" corresponding to the atmospheric air pressure appears at the outlet 9 of the pulser 10 at the moment of time $t_2$ (FIG. 3*b*).

When the pneumatic signal "0" appears at the outlet 9 of the pulser 10, the air is discharged through the open nozzle 86 into the atmosphere through the pipes 59 and 60 from the chamber 55 of the switching element 7, through the pipe 195 from the chamber 194 of the switching element 32, through the pipe 182 from the chamber 181 of the switch 29, through the pipe 176 from the chamber 175 of the switch 41 and, with a certain time delay, through the pipe 90 and throttle 128 from the chamber 127 of the switching element 16.

As a result, the rod 52 of the switching element 7 rises because the pressure head (0.6 kg/cm$^2$ approximately) in the chamber 56 rises above the atmospheric air pressure in the chamber 54. The nozzle 58 closes thus cutting off the supply of pure air from the source 49 into the chamber 54 and into the receiving pipe 4 of the jet sensor 1 communicating with said chamber 54. The analyzed gas (the air of the industrial building) begins to be drawn through the pipe 45 and filter 46, then through the feed pipe 3 and the receiving pipe 4.

As the pneumatic signal "0" enters the chamber 181 of the switch 29, the rod 187 goes down, closing the nozzle 156 and cutting off the chamber 154 of the pressure adder 25 from the pneumatic container 188. The pressure of air in the chamber 154 of the pressure adder 25 communicating with the nozzle 156 is maintained at the level $p_1$ previously reached within the time interval $(t_2 - t_1)$, the absolute value of this air pressure being equal to the vacuum in the body 2 of the jet sensor 1, of the corresponding working point.

It follows from the above that the pneumatic detector according to the invention functions steadily during the correction cycle of the working point. Therefore, it can be made with a jet sensor 1 possessing a steep static curve and, consequently, a high sensitivity. Steady operation of the detector is ensured by providing the vacuum former 24 with a pressure adder 25 whose inlet 26 (FIG. 1) is connected to the integrator 30 which ensures a smooth increase of the vacuum in the body 2 of the jet sensor 1. Owing to the connection between the outlet of the pressure comparator 12 and the control inlet 23 of the pulser 10 and to the connection between the outlet 9 of the pulser 10 and the switch 29, the pressure adder 25 memorizes the required vacuum of the corresponding working point.

As the pneumatic signal "0" enters the chamber 194 of the switching element 32, the rod 198 rises, thus closing the nozzle 199 and opening the nozzle 200. As a result, the air pressure in the chamber 190 communicating with the reference pressure setter 37 becomes equal to the pressure set by the setter 37 (0.22 kg/cm$^2$ approximately).

When the pneumatic signal "0" enters the chamber 175 of the switch 41, the rod 180 rises, closing the nozzle 174 and cutting off the central point A of the pressure divider 38 from the atmosphere. The air pressure in the central point A of the pressure divider 38 becomes equal to $kP_2$., where $P_2$ is the air pressure set by the reference pressure setter 14 and the coefficient $K = R_2/(R_1+R_2)$, where $R_1$ and $R_2$ represent the pneumatic resistances of the throttles 170 and 171, respectively.

The value of $kP_2$ is the minimum level of the indicated dangerous concentration of gas and vapour contaminants in the air of industrial buildings. This level may be as low as necessary.

Thus, owing to the provision of the pressure divider 38 in the vacuum former 24, the pneumatic detector according to the invention can be used to determine the concentrations of gas and vapour contaminants in the air of industrial buildings of any size.

The air at a pressure $kP_2$ flows through the pipe 158 into the chamber 157 of the pressure adder 25.

Under the effect of the above-described processes the air pressure in the chambers 154 and 157 settles at the levels $P_1$ and $kP_2$, respectively. Then the vacuum in the chamber 159 and in the body 2 of the jet sensor 1 becomes equal to $(P_1 - kP_2)$, as shown in FIG. 3*g*. This vacuum will correspond no longer to the value at which the laminar flow of air turns into a turbulent flow in the gap between the feed pipe 3 and the receiving pipe 4, but will correspond to its laminar flow. The vacuum at the outlet from the receiving pipe 4 and, consequently, in the chamber 106 of the pressure comparator 12 communicating with said pipe drops below the pressure in its chamber 104 set by the reference pressure setter 14. As a result, the rod 100 rises, closing the nozzle 110 and cutting of the chambers 102 and 107 from the compressed air source 49. The pneumatic signal "0" (FIG. 3*i*) appears at the outlets of the pressure comparator 12.

When the pneumatic signal "0" is delivered from the outlet 9 (FIG. 2) of the pulser 10 with a time delay $\Delta t$ ensured by the throttle 128 into the chamber 127 of the switching element 16, the rod 130 rises because the pressure in the chamber 129 communicating via the pipe 211 with the outlet 62 of the setter 63 rises above the pressure in the chamber 127. The nozzle 131 closes, whereas the nozzle 129 opens. The chambers 102 and 107 of the pressure comparator 12 are put in communication with the chamber 143 of the output relay 20 through the open nozzle 141. The nozzle 152 remains closed and the pneumatic signal "0" (FIG. 3*j*) is produced at the output of the relay 20.

The fact that the pneumatic signal "0" is delivered to the switching element 16 (FIG. 2) with a time delay $\Delta t$, i.e. when the pneumatic signal "0" has already settled at the outlet of the pressure comparator 12, prevents erroneous operation of the output relay 20. The same time delay protects the pneumatic detector against the erroneous termination of the working point correction cycle if said cycle begins when the pneumatic detector produces at its outlet a signal indicating a dangerous concentration of gas and vapour contaminants in the air of industrial buildings.

If a dangerous concentration of gas and vapour contaminants appears in the analyzed gas in the course of the measuring cycle whose duration is, say, $T = t_5 - t_2$ (FIG. 3*j*) and this occurs at a moment of time, say $t_3$, this will be accompanied by turbulization of jet of the analyzed gas flowing from the receiving pipe 4 (FIG. 2). As a result, the absolute pressure at the outlet of the receiving pipe 4 drops sharply as shown in FIG. 3*h*. The vacuum at its outlet and in the chamber 106 (FIG. 2) of the pressure comparator 12 becomes lower than the air pressure in its chamber 104. When the air pressure in the chamber 104 becomes higher than the vacuum in the chamber 106, the rod 100 goes down, closing the nozzle 111 and opening the nozzle 110. The chambers 102 and 106 communicate through the open nozzle 110 with the compressed air source 49 and the pressure of air in said chambers becomes approximately equal to the supply pressure as shown in FIG. 3*i*.

The air at the supply pressure flows from the chambers 102 and 107 through the pipe 123 into the chambers 124 and 125 of the switching element 16. The nozzle 131 remains closed and the nozzle 141, open. The air at supply pressure flows through the open nozzle 141 and the pipe 142 into the chamber 143 of the output relay 20. The rod 151 goes down, closing the nozzle 145 and opening the nozzle 152. The chamber 144 is put in communication with the source 49 and the compressed air at supply pressure flows through the pipes 147 and 148 into the pneumatic detector 146 and the latter operates. The danger signal (air at supply pressure, FIG. 3*j*) appears at the outlet of the relay 20, said outlet being formed by the outlet from the chamber 144.

When the dangerous concentration of gas and vapour contaminants in the air of industrial buildings vanishes, for example at the moment of time $t_4$, the turbulization of the air jet discharged from the receiving pipe 4 ceases, the absolute pressure at its outlet grows as shown in FIG. 3*h*, the rod 100 of the pressure comparator 12 rises, closing the nozzle 110 and opening the nozzle 111, and the air pressure at the outlet of the pressure comparator 12 becomes equal to the atmospheric pressure as shown in FIG. 3*i*. The chamber 143 of the output relay 20 is vented to the atmosphere through the pipe 142, open nozzle 141 chamber 129, pipe 123, chamber 107 and the open nozzle 111. The air pressure in the chamber 143 drops, the rod 151 rises, closing the nozzle 152 and opening the nozzle 145. The outlet of the relay 20 is put in communication with the atmosphere through the open nozzle 145 and the air pressure at the outlet of the relay 20 becomes equal to zero as shown in FIG. 3*j*. The pneumatic detector is cut off.

The next correction cycle of the working point begins at the moment of time $t_5$ while the next cycle of direct analysis of air in the industrial building begins at the moment of time $t_6$, both cycles proceeding as described above.

Periodical corrections of the working point are necessitated by the changes in the physical parameters of the analyzed and reference gases, such as temperature, humidity and barometric pressure.

The pneumatic detector of gas and vapour contaminants in the air of industrial buildings according to the invention makes it possible to determine different dangerous concentrations of these contaminants with a high degree of accuracy and reliability.

We claim:

1. A pneumatic detector of gas and vapor contaminants in the air of industrial buildings comprising:

a jet sensor having
a body,
a feed pipe and
a receiving pipe, the feed pipe and the receiving pipe being accommodated in said body;
a reference gas channel conducting a reference gas into said feed pipe;
an analyzed gas channel conducting air of industrial buildings into said feed pipe;
a first switching element with three inlets and an outlet, the first inlet being connected to said reference gas channel, the second inlet being connected to said analyzed gas channel, and the outlet of said first switching element communicating with said feed pipe;
a pulser whose outlet is connected to the third inlet of said first switching element and which serves as an element for setting the operational mode;
a pressure comparator with two inlets and an outlet, the first inlet being connected with said receiving pipe;
a first reference pressure setter communicating with the second inlet of said pressure comparator;
a second switching element with two inlets and two outlets, the first inlet communicating with said outlet of said pressure comparator;
a delay unit having an inlet and an outlet, the outlet being in communication with the second inlet of said second switching element, the inlet being in communication with the outlet of said pulser;
an output relay whose inlet is connected to the first outlet of said second switching element;
a first switch having a control inlet and an outlet, the control inlet being connected to the second outlet of said second switching element, the outlet communicating with an inlet of said pulser;
a vacuum former for building up a vacuum in said body of said jet sensor;
a pressure adder, which is an element of said vacuum former, provided with three inlets and an outlet, the first inlet communicating with an inner space of said body of said jet sensor;
a second switch, which is an element of said vacuum former, having an inlet, a control inlet and an outlet, the outlet being connected to said second inlet of said pressure adder, the control inlet of said second switch being connected to the outlet of said pulser;
an integrator, which is an element of said vacuum former, having an inlet and an outlet, the outlet being connected to said inlet of said second switch;
a third switching element, which is an element of said vacuum former, having two inlets, a control inlet and one outlet, the outlet being connected to the inlet of said integrator, the control inlet being connected to said outlet of said pulser;
a second reference pressure setter, which is an element of said vacuum former, connected to said first inlet of said third switching element;
a third reference pressure setter, which is an element of said vacuum former, connected to said second inlet of said third switching element;
a pressure divider, which is an element of said vacuum former, having a central point, which communicates with said third inlet of said pressure adder, an inlet, which communicates with the first reference pressure setter, and an outlet, which is vented to the atmosphere;
a third switch, which is an element of said vacuum former, having a control inlet connected to the outlet of said pulser, an inlet communicating with the central point of said pressure divider, and an outlet communicating with the atmosphere;
an amplifier whose inlet is connected to the outlet of said pressure adder; and a vacuum pump connected to an outlet of said amplifier and communicating with the inner space of said body of said jet sensor.

2. A pneumatic detector of gas and vapor contaminants in the air of industrial buildings according to claim 1, wherein said analyzed gas channel comprises: a first pipe communicating with said feed pipe; and a filter in working relation with said first pipe.

3. A pneumatic detector of gas and vapor contaminants in the air of industrial buildings according to claim 1, wherein said reference gas channel comprises: a second pipe communicating with said feed pipe; and a first throttle in working relation with said second pipe.

4. A pneumatic detector of gas and vapor contaminants in the air of industrial buildings according to claim 2, wherein said reference gas channel comprises: a second pipe communicating with said feed pipe; and a first throttle in working relation with said second pipe.

5. A pneumatic detector of gas and vapor contaminants in the air of industrial buildings according to claim 1, wherein said first switching element comprises: a first and a second membrane, said membranes being of different areas, said membranes defining first, second and third compartments; a rod interconnecting said membranes; a first end of said rod located in said first chamber, said first end of said rod serving as a shutter for a nozzle, said nozzle communicating with said outlet of said pulser; said second chamber serving as said third inlet of said first switching element; an outlet of a pressure head setter communicating with said third chamber of said first switching element; said first chamber communicating with said reference gas channel.

6. A pneumatic detector of gas and vapor contaminants in the air of industrial buildings according to claim 4, wherein said first switching element comprises: a first and a second membrane, said membranes being of different areas, said membranes defining first, second and third compartments; a rod interconnecting said membranes; a first end of said rod located in said first chamber, said first end of said rod serving as a shutter for a nozzle, said nozzle communicating with said outlet of said pulser; said second chamber serving as said third inlet of said first switching element; an outlet of a pressure head setter communicating with said third chamber of said first switching element; said first chamber communicating with said reference gas channel.

7. A pneumatic detector of gas and vapor contaminants in the air of industrial buildings according to claim 6, wherein said pressure head setter comprises: a casing; a membrane accomodated in said casing and defining first and second compartments; a spring accomodated in said first chamber and being connected to said membrane; a screw for adjusting the tension of said spring; the center of said membrane serving as a shutter for a nozzle, said nozzle communicating with the atmosphere; a pipe connecting said second chamber and a compressed air source; and a constant-flow throttle installed on said pipe; the second chamber communicating with an outlet of said pressure head setter.

8. A pneumatic detector of gas and vapor contaminants in the air of industrial buildings according to claim 1, wherein said pulser comprises: a first, a second and a third membrane, said membranes defining first, second, third and fourth compartments; a rod interconnecting said membranes; a first end of said rod accomodated in said first compartment serves as a first shutter for a first nozzle, said first nozzle communicating with a compressed air source; a second end of said rod accomodated in said fourth compartment serves as a second shutter for a second nozzle, said second nozzle communicating with said first chamber and through a variable-resistance throttle with said third chamber; said second chamber communicating with an outlet of a pressure head setter; said first chamber communicating with said outlet of said pulser.

9. A pneumatic detector of gas and vapor contaminants in the air of industrial buildings according to claim 7, wherein said pulser comprises: a first, a second and a third membrane, said membranes defining first, second, third and fourth compartments; a rod interconnecting said membranes; a first end of said rod accomodated in said first compartment serves as a first shutter for a first nozzle, said first nozzle communicating with said compressed air source; a second end of said rod accomodated in said fourth compartment serves as a second shutter for a second nozzle, said second nozzle communicating with said first chamber and through a variable-resistance throttle with said third chamber; said second chamber communicating with an outlet of a pressure head setter; said first chamber communicating with said outlet of said pulser.

10. A pneumatic detector of gas and vapor contaminants in the air of industrial buildings according to claim 1, wherein said pressure comparator comprises: first, second, third, fourth and fifth membranes, said membranes defining first, second, third, fourth, fifth and sixth compartments; a rod interconnecting said membranes; a first end of said rod accomodated in said first compartment and serving as a first shutter for a first nozzle, said first nozzle communicating with a compressed air source; a second end of said rod accomodated in said sixth compartment and serving as a second shutter for a second nozzle, said second nozzle and said second and said fourth compartment communicating with the atmosphere; said first inlet of said pressure comparator communicating with said fifth compartment; said second inlet of said pressure comparator communicating with said third compartment; said outlet of said pressure comparator communicating with said first and with said second compartments.

11. A pneumatic detector of gas and vapor contaminants in the air of industrial buildings according to claim 9, wherein said pressure comparator comprises: first, second, third, fourth and fifth membranes, said membranes defining first, second, third, fourth, fifth and sixth compartments; a rod interconnecting said membranes; a first end of said rod accomodated in said first compartment and serving as a first shutter for a first nozzle, said first nozzle communicating with said compressed air source; a second end of said rod accomodated in said sixth compartment and serving as a second shutter for a second nozzle, said second nozzle and said second and said fourth compartment communicating with the atmosphere; said first inlet of said pressure comparator communicating with said fifth compartment; said second inlet of said pressure comparator communicating with said third compartment; said outlet of said pressure comparator communicating with said first and with said second compartments.

12. A pneumatic detector of gas and vapor contaminants in the air of industrial buildings according to claim 1, wherein said first reference pressure setter comprises: a membrane defining first and second compartments, said second compartment communicating with said second inlet of said pressure comparator; a spring accomodated in said first compartment and being connected to said membrane; a screw for adjusting the tension of said spring; the center of said membrane serving as a shutter for a nozzle, said nozzle communicating with the atmosphere; a pipe connecting said second compartment and a compressed air source; and a constant-flow throttle installed on said pipe.

13. A pneumatic detector of gas and vapor contaminants in the air of industrial buildings according to claim 11, wherein said first reference pressure setter comprises: a membrane defining first and second compartments, said second compartment communicating with said second inlet of said pressure comparator; a spring accomodated in said first compartment and being connected to said membrane; a screw for adjusting the tension of said spring; the center of said membrane serving as a shutter for a nozzle, said nozzle communicating with the atmosphere; a pipe connecting said second compartment and said compressed air source; and a constant-flow throttle installed on said pipe.

14. A pneumatic detector of gas and vapor contaminants in the air of industrial buildings according to claim 1, wherein said second switching element comprises: first, second and third membranes, said membranes defining first, second, third and fourth compartments; a bar interconnecting said membranes; a first end of said bar accomodated in said first compartment serving as a first shuttle for a first nozzle, said first nozzle communicating with said control inlet of said first switch and serving as said second outlet of said second switching element; a second end of said bar accomodated in said fourth compartment serving as a second shutter for a second nozzle, said second nozzle communicating with said inlet of said output relay and serving as said first outlet of said second switching element; said third compartment communicating with an outlet of a pressure head setter; said second inlet of said second switching element communicating with said second compartment; said first inlet of said second switching element communicating with said first and said fourth compartments.

15. A pneumatic detector of gas and vapor contaminants in the air of industrial buildings according to claim 13, wherein said second switching element comprises: first, second and third membranes, said membranes defining first, second, third and fourth compartments; a bar interconnecting said membranes; a first end of said bar accomodated in said first compartment serving as a first shutter for a first nozzle, said first nozzle communicating with said control inlet of said first switch and serving as said second outlet of said second switching element; a second end of said bar accomodated in said fourth compartment serving as a second shutter for a second nozzle, said second nozzle communicating with said inlet of said output relay and serving as said first outlet of said second switching element; said third compartment communicating with said outlet of said pressure head setter; said second inlet of said second switching element communicating with said second compartment; said first inlet of said second switching communicating with said first and said fourth compartments.

16. A pneumatic detector of gas and vapor contaminants in the air of industrial buildings according to claim 1, wherein said delay unit is a constant-flow throttle.

17. A pneumatic detector of gas and vapor contaminants in the air of industrial buildings according to claim 15, wherein said delay unit is a constant-flow throttle.

18. A pneumatic detector of gas and vapor contaminants in the air of industrial buildings according to claim 1, wherein said output relay unit comprises: first, second and third membranes defining first, second, third and fourth compartments, said second compartment communicating with said inlet of said outlet relay unit, said third compartment communicating with an outlet of a pressure head setter, said fourth compartment communicating with the atmosphere; a pneumatic indicator communicating with said first compartment; a rod interconnecting said membranes; a first end of said rod accomodated in said first compartment serving as a first shutter for a first nozzle, said first nozzle communicating with a compressed air source; a second end of said rod accomodated in said fourth compartment serving as a second shutter for a second nozzle, said second nozzle communicating with said pneumatic indicator.

19. A pneumatic detector of gas and vapor contaminants in the air of industrial buildings according to claim 17, wherein said output relay unit comprises: first, second and third membranes, said membranes defining first, second, third and fourth compartments, said second compartment communicating with said inlet of said outlet relay unit, said third compartment communicating with said outlet of said pressure head setter, said fourth compartment communicating with the atmosphere; a pneumatic indicator communicating with said first compartment; a rod interconnecting said membranes; a first end of said rod accomodated in said first compartment serving as a first shutter for a first nozzle, said first nozzle communicating with said compressed air source; a second end of said rod accomodated in said fourth compartment serving as a second shutter for a second nozzle, said second nozzle communicating with said pneumatic indicator.

20. A pneumatic detector of gas and vapor contaminants in the air of industrial buildings according to claim 1, wherein said first switch comprises: first and second membranes, said membranes defining first, second and third compartments, said third compartment communicating with an outlet of a pressure head setter, said second compartment communicating with said second outlet of said second switching element, said first compartment communicating with said inlet of said pulser; a rod interconnecting said membranes; a first end of said rod accomodated in said first compartment serving as a shutter for a nozzle, said nozzle communicating with a compressed air source.

21. A pneumatic detector of gas and vapor contaminants in the air of industrial buildings according to claim 19, wherein said first switch comprises: first and second membranes, said membranes defining first, second and third compartments, said third compartment communicating with said outlet of said pressure head setter, said second compartment communicating with said second outlet of said second switching element, said first compartment communicating with said inlet of said pulser; a rod interconnecting said membranes; a first end of said rod accomodated in said first compartment serving as a shutter for a nozzle, said nozzle communicating with said compressed air source.

22. A pneumatic detector of gas and vapor contaminants in the air of industrial buildings according to claim 1, wherein said pressure adder comprises: first, second, third, fourth and fifth membranes, said membranes defining first, second, third, fourth, fifth and sixth compartments, said first and said sixth compartments communicating with said outlet of said pressure adder, said second compartment communicating with said third inlet of said pressure adder, said third compartment communicating with said second inlet of said pressure adder, said fourth compartment communicating with said first inlet of said pressure adder, said fifth compartment communicating with the atmosphere; a rod interconnecting said membranes; a first end of said rod accomodated in said first compartment serving as a first shutter for a first nozzle, said first nozzle communicating with a compressed air source; and a second end of said rod accomodated in said sixth compartment serving as a second shutter for a second nozzle, said second nozzle communicating with the atmosphere.

23. A pneumatic detector of gas and vapor contaminants in the air of industrial buildings according to claim 21, wherein said pressure adder comprises: first, second, third, fourth and fifth membranes, said membranes defining first, second, third, fourth, fifth and sixth compartments, said first and said sixth compartments communicating with said outlet of said pressure adder, said second compartment communicating with said third inlet of said pressure adder, said third compartment communicating with said second inlet of said pressure adder, said fourth compartment communicating with said first inlet of said pressure adder, said fifth compartment communicating with the atmosphere; a rod interconnecting said membranes; a first end of said rod accomodated in said first compartment serving as a first shutter for a first nozzle, said first nozzle communicating with said compressed air source; and a second end of said rod accomodated in said sixth compartment serving as a second shutter for a second nozzle, said second nozzle communicating with the atmosphere.

24. A pneumatic detector of gas and vapor contaminants in the air of industrial buildings according to claim 1, wherein said pressure divider comprises: a variable pneumatic resistance throttle having a first and a second end, said first end serving as said inlet of said pressure divider, said second end serving as said central point of said pressure divider; and a throttle having one end connected to said central point of said pressure divider and the other end serving as said outlet of said pressure divider.

25. A pneumatic detector of gas and vapor contaminants in the air of industrial buildings according to claim 23, wherein said pressure divider comprises: a variable pneumatic resistance throttle having a first and a second end, said first end serving as said inlet of said pressure divider, said second end serving as said central point of said pressure divider; and a throttle having one end connected to said central point of said pressure divider and the other end serving as said outlet of said pressure divider.

26. A pneumatic detector of gas and vapor contaminants in the air of industrial buildings according to claim 1, wherein said third switch comprises: first and second membranes, said membranes defining first, second and third compartments, said first compartment communicating with the atmosphere, said second compartment communicating with said control inlet of said third switch, said third compartment communicating with an outlet of a pressure head setter; a rod interconnecting said membranes; an end of said rod accomodated in said first compartment serving as a shutter for a nozzle, said nozzle communicating with said inlet of said third switch.

27. A pneumatic detector of gas and vapor contaminants in the air of industrial buildings according to claim 25, wherein said third switch comprises: first and second membranes, said membranes defining first, second and third compartments, said first compartment communicating with the atmosphere, said second compartment communicating with said control inlet of said third switch, said third compartment communicating with said outlet of said pressure head setter; a rod interconnecting said membranes; an end of said rod accomodated in said first compartment serving as a shutter for a nozzle, said nozzle communicating with said inlet of said third switch.

28. A pneumatic detector of gas and vapor contaminants in the air of industrial buildings according to claim 1, wherein said second switch comprises: first and second membranes, said membranes defining first, second and third compartments, said first compartment communicating with an outlet of a pressure head setter, said second compartment communicating with said control inlet of said second switch, said third compartment communicating with said inlet of said second switch; a rod interconnecting said membranes; an end of said rod accomodated in said third compartment serving as a shutter for a nozzle, said nozzle communicating with said outlet of said second switch.

29. A pneumatic detector of gas and vapor contaminants in the air of industrial buildings according to claim 27, wherein said second switch comprises: first and second membranes, said membranes defining first, second and third compartments, said first compartment communicating with said outlet of said pressure head setter, said second compartment communicating with said control inlet of said second switch, said third compartment communicating with said inlet of said second switch; a rod interconnecting said membranes; an end of said rod accomodated in said third compartment serving as a shutter for a nozzle, said nozzle communicating with said outlet of said second switch.

30. A pneumatic detector of gas and vapor contaminants in the air of industrial buildings according to claim 1, wherein said integrator comprises: a pneumatic container having a first and a second end, said second end serving as said outlet of said integrator; and a variable pneumatic resistance throttle having a first and a second end, said first end serving as said inlet of said integrator, said second end being connected to said first end of said pneumatic container.

31. A pneumatic detector of gas and vapor contaminants in the air of industrial buildings according to claim 29, wherein said integrator comprises: a pneumatic container having a first and a second end, said second end serving as said outlet of said integrator; and a variable pneumatic resistance throttle having a first and a second end, said first end serving as said inlet of said integrator, said second end being connected to said first end of said pneumatic container.

32. A pneumatic detector of gas and vapor contaminants in the air of industrial buildings according to claim 1, wherein said third switching element comprises: first, second and third membranes, said membranes defining first, second, third and fourth compartments, said first compartment communicating with said outlet of said third switching element, said second compartment communicating with said control inlet of said third switching element, said third compartment communicating with an outlet of a pressure head setter; a bar interconnecting said membranes; a first end of said bar accomodated in said first compartment serving as a first shutter for a first nozzle, said first nozzle communicating with a compressed air source; a second end of said bar accomodated in said fourth compartment serving as a second shutter for a second nozzle, said second nozzle communicating with said third reference pressure setter.

33. A pneumatic detector of gas and vapor contaminants in the air of industrial buildings according to claim 31, wherein said third switching element comprises: first, second and third membranes, said membranes defining first, second, third, and fourth compartments, said first compartment communicating with said outlet of said third switching element, said second compartment communicating with said control inlet of said third switching element, said third compartment communicating with said outlet of said pressure head setter, said fourth compartment communicating with said second end of said pneumatic container; a bar interconnecting said membranes; a first end of said bar accomodated in said first compartment serving as a first shutter for a first nozzle, said first nozzle communicating with said compressed air source; a second end of said bar accomodated in said fourth compartment serving as a second shutter for a second nozzle; said second nozzle communicating with said third reference pressure setter.

34. A pneumatic detector of gas and vapor contaminants in the air of industrial buildings according to claim 1, wherein said third reference pressure setter comprises: a membrane defining a first and a second compartment, said second compartment communicating with said second inlet of said third switching element; a spring accomodated in said first chamber and being connected to said membranes; a screw for adjusting the tension of said spring; the center of said membrane serving as a shutter for a nozzle, said nozzle communicating with the atmosphere; a pipe connecting said second compartment and a compressed air source; and a constant-flow throttle installed on said pipe.

35. A pneumatic detector of gas and vapor contaminants in the air of industrial buildings according to claim 33, wherein said third reference pressure setter comprises: a membrane defining a first and a second compartment, said second compartment communicating with said second inlet of said third switching element; a spring accomodated in said first chamber and being connected to said membrane; a screw for adjusting the tension of said spring; the center of said membrane serving as a shutter for a nozzle, said nozzle communicating with the atmosphere; a pipe connecting said second compartment and said compressed air source; and a constant-flow throttle installed on said pipe.

* * * * *